(12) United States Patent
Sakai et al.

(10) Patent No.: US 11,426,342 B2
(45) Date of Patent: Aug. 30, 2022

(54) HAIR COSMETIC

(71) Applicant: KAO CORPORATION, Tokyo (JP)

(72) Inventors: Yuta Sakai, Yoshikawa (JP); Hiroshi Yoshida, Utsunomiya (JP); Hiroki Fujinaga, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/765,061

(22) PCT Filed: Nov. 19, 2018

(86) PCT No.: PCT/JP2018/042678
§ 371 (c)(1),
(2) Date: May 18, 2020

(87) PCT Pub. No.: WO2019/098366
PCT Pub. Date: May 23, 2019

(65) Prior Publication Data
US 2020/0360262 A1 Nov. 19, 2020

(30) Foreign Application Priority Data
Nov. 20, 2017 (JP) .............................. JP2017-223221

(51) Int. Cl.
*A61K 8/81* (2006.01)
*A61K 8/49* (2006.01)
*A61Q 5/02* (2006.01)

(52) U.S. Cl.
CPC .............. *A61K 8/817* (2013.01); *A61K 8/492* (2013.01); *A61Q 5/02* (2013.01)

(58) Field of Classification Search
None
See application file for complete search history.

(56) References Cited

U.S. PATENT DOCUMENTS

| | | | |
|---|---|---|---|
| 4,208,183 A | 6/1980 | Grollier et al. | |
| 7,862,625 B2 | 1/2011 | Koike et al. | |
| 2003/0051297 A1 | 3/2003 | Patel et al. | |
| 2003/0074748 A1 | 4/2003 | Patel et al. | |
| 2007/0111897 A1* | 5/2007 | Dahanayake | C09K 8/08 507/211 |
| 2010/0154135 A1 | 6/2010 | Matsunaga et al. | |
| 2010/0170048 A1* | 7/2010 | Koike | A61K 8/492 8/407 |

FOREIGN PATENT DOCUMENTS

| | | |
|---|---|---|
| JP | 63-258403 A | 10/1988 |
| JP | 2004-525130 A | 8/2004 |
| JP | 2007-326802 A | 12/2007 |
| JP | 2008-156254 | 7/2008 |
| JP | 2012-176996 | 9/2012 |
| JP | 2014-24766 A | 2/2014 |
| WO | WO2008-003686 | 1/2008 |
| WO | WO 2008/149535 A1 | 12/2008 |

OTHER PUBLICATIONS

International Search Report dated Dec. 11, 2018 in PCT/JP2018/042678 filed Nov. 19, 2018, 1 page.
U.S. Appl. No. 16/765,033, filed May 18, 2020, Yoshida, Hiroshi et al.
U.S. Appl. No. 16/765,046, filed May 18, 2020, Nagayama, Ayami.
U.S. Appl. No. 16/765,038, filed May 18, 2020, Shimzau, Ayako et al.
U.S. Appl. No. 16/765,067, filed May 18m 2020, Shimzu, Ayako et al.
Extended European Search Report dated Jul. 30, 2021, in European patent application No. 18879282.4—8 pages.

* cited by examiner

*Primary Examiner* — Melissa L Fisher
(74) *Attorney, Agent, or Firm* — Oblon, McClelland, Maier & Neustadt, L.L.P.

(57) ABSTRACT

The present invention relates to a hair cosmetic containing the following components (A) to (C):
(A) a compound represented by the following general formula (1) or a salt thereof:

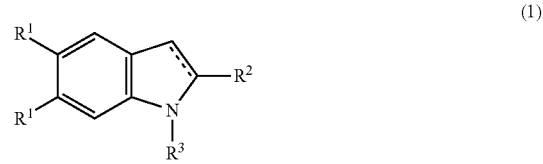

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;
(B) a cationic polymer; and
(C) an ampholytic polymer having a predetermined cationic structural unit and an anionic structural unit,
a mass ratio of the component (C) to the component (A) [(C)/(A)] being 0.7 or more and 10 or less.

15 Claims, No Drawings

HAIR COSMETIC

FIELD OF THE INVENTION

The present invention relates to a hair cosmetic.

BACKGROUND OF THE INVENTION

Conventionally, as a hair dye for gray hair dyeing, an air-oxidative hair dye using 5,6-dihydroxyindole, 5,6-dihydroxyindoline, or a derivative thereof, each of which is a melanin precursor, is known. Such a melanin precursor does not use an oxidizing agent, and therefore, even in the case of being used for a hair dye, it is less in damage of the hair, and it is high in convenience as a dye for hair dye.

For example, PTL 1 discloses an aerosol type one-part hair dye composition containing the aforementioned melanin precursor, an aromatic alcohol, a predetermined polyethoxylate, and a thickening polymer, which is favorable in hair dyeing properties. PTL 2 discloses a dyeable composition for hair containing at least 5,6-dihydroxyindole and at least 0.1% by weight of a foam generator, which is packaged under pressure in an aerosol device under a predetermined condition.

CITATION LIST

Patent Literature

PTL 1: JP 2007-326802 A
PTL 2: JP S63-258403 A

SUMMARY OF THE INVENTION

The present invention relates to the following [1] to [2].

[1] A hair cosmetic containing the following components (A) to (C):

(A) a compound represented by the following general formula (1) or a salt thereof:

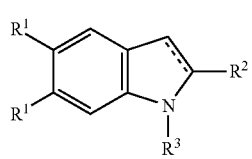

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) a cationic polymer; and (C) an ampholytic polymer having at least one cationic structural unit selected from the group consisting of a structural unit represented by the following general formula (2) and a structural unit represented by the following general formula (3), and an anionic structural unit:

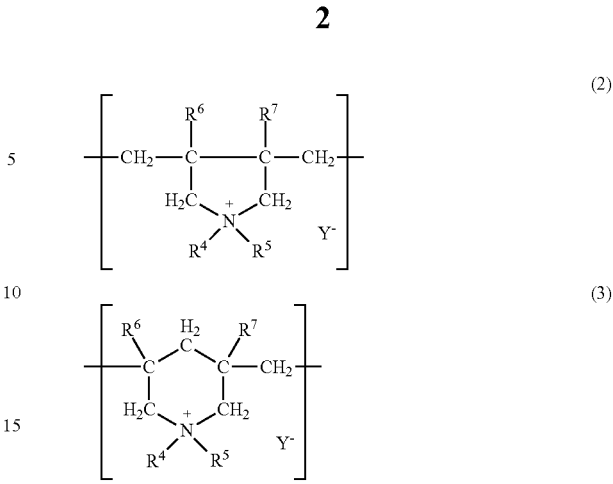

wherein $R^4$ and $R^5$ each independently represent a hydrogen atom, an alkyl group having 1 or more and 18 or less carbon atoms, an aryl group, a hydroxyalkyl group, an amidoalkyl group, a cyanoalkyl group, an alkoxyalkyl group, or a carboalkoxyalkyl group; $R^6$ and $R^7$ each independently represent a hydrogen atom, an alkyl group having 1 or more and 3 or less carbon atoms, or a phenyl group; and $Y^-$ represents an anion, a mass ratio of the component (C) to the component (A) [(C)/(A)] being 0.7 or more and 10 or less.

[2] A dyeing method of hair including a step of applying the hair cosmetic as set forth in the above [1] on hair.

DETAILED DESCRIPTION OF THE INVENTION

Hair Cosmetic

The hair cosmetic of the present invention contains the following components (A) to (C):

(A) a compound represented by the following general formula (1) or a salt thereof:

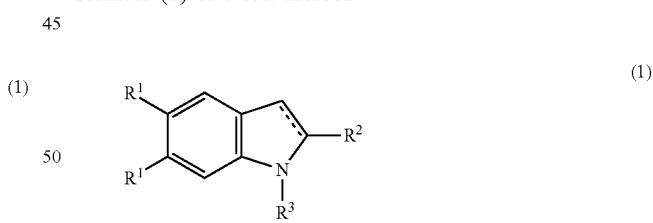

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) a cationic polymer; and (C) an ampholytic polymer having at least one cationic structural unit selected from the group consisting of a structural unit represented by the following general formula (2) and a structural unit represented by the following general formula (3), and an anionic structural unit:

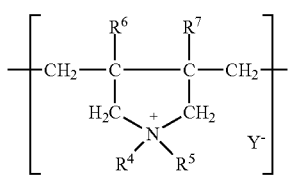

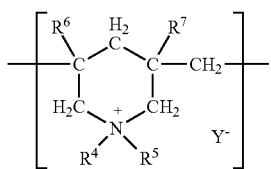

wherein $R^4$ and $R^5$ each independently represent a hydrogen atom, an alkyl group having 1 or more and 18 or less carbon atoms, an aryl group, a hydroxyalkyl group, an amidoalkyl group, a cyanoalkyl group, an alkoxyalkyl group, or a carboalkoxyalkyl group; $R^6$ and $R^7$ each independently represent a hydrogen atom, an alkyl group having 1 or more and 3 or less carbon atoms, or a phenyl group; and $Y^-$ represents an anion, a mass ratio of the component (C) to the component (A) [(C)/(A)] being 0.7 or more and 10 or less.

It may not be said that the aforementioned melanin precursor-containing hair dye is satisfactory in hair dyeing properties as compared with typical oxidative hair dyes, and it is desired that the hair dyeing properties are more improved. In addition, though the techniques disclosed in PTLs 1 and 2 are a technique regarding the hair dye, on use of a hair dye, a lot of time and energy are spent, such that a care for preventing staining of a place where hair dyeing is carried out, such as a bathroom and a lavatory, is needed, so that it may not be said that the foregoing technique is a daily simply usable, and a long period of time is required in order to obtain a hair dyeing effect to some extent.

Then, the present inventors thought that by blending the aforementioned melanin precursor in a hair cosmetic, such as a shampoo and a hair treatment, which is capable of being daily used in a bathroom, high hair dyeing properties can be exhibited simply and for a short period of time, and made investigations.

In a so-called in-bath hair care product to be used in a bathroom, it is typical to use a cationic substance, such as a cationic polymer, in order to make the touch of the hair during applying on the hair or after drying favorable and to reduce damage of the hair. However, it has become clear that since 5,6-dihydroxyindole, 5,6-dihydroxyindoline, or a derivative thereof, each of which is a melanin precursor, manifests anionic properties in an alkaline region having hair dyeing properties, it forms a complex together with the cationic substance, to generate precipitation. When the precipitation is generated, not only storage stability or appearance of the product is impaired, but also it becomes difficult to penetrate sufficient amounts of the active ingredients into the hair.

A problem of the present invention is to provide a hair cosmetic which contains a predetermined melanin derivative and a cationic polymer and which even when stored for a long period of time, does not generate precipitation and reveals excellent storage stability and appearance.

The present inventors have found that the aforementioned problem can be solved by a hair cosmetic containing a predetermined melanin derivative, a cationic polymer, and a predetermined ampholytic polymer.

The hair cosmetic of the present invention is free from generation of precipitation to be caused owing to complex formation between a melanin precursor and a cationic polymer and favorable in storage stability and appearance.

In the present invention, examples of the hair cosmetic include a hair conditioning agent, a styling agent, and a hair dye, in addition to a hair cleansing agent, such as a shampoo. Of these, a hair cleansing agent is preferred from the viewpoint of obtaining the effects of the present invention and the viewpoint of enabling one to simply achieve hair dyeing through a daily hair care behavior. The formulation of the hair cosmetic is not particularly limited, and it is possible to take an arbitrary formulation, for example, a liquid, a foam, a paste, a cream, a solid, and a powder. For example, in the case of a hair cleansing agent, the formulation is preferably a liquid, a paste, or a cream, and more preferably a liquid.

Even when the hair cosmetic of the present invention contains both the component (A) that is the melamine precursor and the component (B) that is the cationic polymer, it is free from generation of precipitation to be caused owing to complex formation between these components and favorable in storage stability.

As a result of investigations made by the present inventors, it has been found that in the hair cosmetic containing the component (A) and the component (B), when using the component (C) that is the ampholytic polymer having a specified structure, an aggregate produced owing to an interaction between the component (A) and the component (B) can be dispersed in the hair cosmetic and dissolved therein.

As for an ampholytic substance capable of suppressing aggregation to be caused owing to complex formation between the component (A) and the component (B), it may be considered to be required such that in addition to the fact that the ampholytic substance has an cation group and an anion group, it is able to selectively hydrophobically interact with an indole structure and/or an indoline structure, and/or a catechol site in the component (A). For that reason, it may be considered that the component (C) that is the ampholytic polymer, in which on the molecular size and molecular structure, at least one cationic structural unit selected from the group consisting of the structural unit represented by the general formula (2) and the structural unit represented by the general formula (3) exists, and an anionic hydrophilic group exists in the vicinity thereof, is able to effectively exhibit the effects of the present invention.

Component (A)

The hair cosmetic of the present invention contains the component (A) that is a compound represented by the following general formula (1) or a salt thereof. The component (A) is a melanin precursor which is polymerized through air oxidation and converted into a melanin pigment and acts as a dyeing agent of hair.

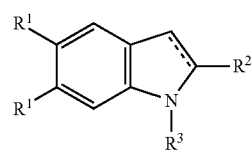

In the formula, a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group.

The melanin precursor of the component (A) is an indole derivative or an indoline derivative that is the compound represented by the general formula (1), or a salt thereof, and in the present invention, one or a combination of two or more thereof can be used. From the viewpoint of hair dyeing properties, the component (A) is more preferably an indole derivative (namely, a π bond exists in the broken line portion in the general formula (1)).

From the viewpoint of availability and hair dyeing properties of the component (A), in the general formula (1), $R^1$ is preferably a hydroxy group; $R^2$ is preferably a hydrogen atom or —COOR (R is a hydrogen atom, a methyl group, or an ethyl group), and more preferably a hydrogen atom or —COOH; and $R^3$ is preferably a hydrogen atom.

Examples of the compound represented by the general formula (1) include 5,6-dihydroxyindole, 5,6-dihydroxyindole-2-carboxylic acid, methyl 5,6-dihydroxyindole-2-carboxylate, ethyl 5,6-dihydroxyindole-2-carboxylate, N-methyl-5,6-dihydroxyindole, N-methyl-5,6-dihydroxyindole-2-carboxylic acid, N-ethyl-5,6-dihydroxyindole, N-ethyl-5,6-dihydroxyindole-2-carboxylic acid, N-acetyl-5,6-dihydroxyindole, N-acetyl-5,6-dihydroxyindole-2-carboxylic acid, 5-acetoxy-6-hydroxyindole, 5-acetoxy-6-hydroxyindole-2-carboxylic acid, 5,6-dihydroxyindoline, 5,6-dihydroxyindoline-2-carboxylic acid, methyl 5,6-dihydroxyindoline-2-carboxylate, ethyl 5,6-dihydroxyindoline-2-carboxylate, N-methyl-5,6-dihydroxyindoline, N-methyl-5,6-dihydroxyindoline-2-carboxylic acid, N-ethyl-5,6-dihydroxyindoline, N-ethyl-5,6-dihydroxyindoline-2-carboxylic acid, N-acetyl-5,6-dihydroxyindoline, N-acetyl-5,6-dihydroxyindoline-2-carboxylic acid, 5-acetoxy-6-hydroxyindoline, and 5-acetoxy-6-hydroxyindoline-2-carboxylic acid.

Examples of the salt of the compound represented by the general formula (1) include a hydrochloride, a hydrobromide, a sulfate, a phosphate, an acetate, a propionate, a lactate, and a citrate of the foregoing compounds. Above all, a hydrobromide is preferred from the viewpoint of availability.

In the general formula (1), in the case where $R^2$ is —COOH, examples of the salt of the compound represented by the general formula (1) include carboxylates thereof ($R^2$ is —COO⁻X⁺ (X⁺ is a cation, such as an alkali metal ion, e.g., Na⁺ and K⁺, an alkaline earth metal ion, e.g., Ca⁺ and Mg⁺, and an ammonium ion)).

From the viewpoint of dyeing the hair in a natural color shade, the component (A) is preferably one or more selected from the group consisting of 5,6-dihydroxyindole, 5,6-dihydroxyindole-2-carboxylic acid, 5,6-dihydroxyindoline, and 5,6-dihydroxyindoline-2-carboxylic acid, and salts thereof; more preferably one or more selected from the group consisting of 5,6-dihydroxyindole, 5,6-dihydroxyindole-2-carboxylic acid, and 5,6-dihydroxyindoline hydrobromide; still more preferably one or two selected from the group consisting of 5,6-dihydroxyindole and 5,6-dihydroxyindole-2-carboxylic acid; and yet still more preferably a combination of 5,6-dihydroxyindole and 5,6-dihydroxyindole-2-carboxylic acid.

In the case of use of a combination of 5,6-dihydroxyindole and 5,6-dihydroxyindole-2-carboxylic acid, a molar ratio thereof is preferably in a range of 50/50 to 99/1, more preferably in a range of 80/20 to 99/1, and still more preferably in a range of 85/15 to 95/5. When the molar ratio of 5,6-dihydroxyindole to 5,6-dihydroxyindole-2-carboxylic acid falls within the aforementioned range, finish of the hair after hair dyeing becomes close to a natural color tint.

The molar ratio of 5,6-dihydroxyindole to 5,6-dihydroxyindole-2-carboxylic acid can be quantitatively determined by means of reversed phase HPLC.

From the viewpoint of improvement in hair dyeing properties, the content of the component (A) in the hair cosmetic is preferably 0.05% by mass or more, and more preferably 0.1% by mass or more, and from the viewpoint of economy, it is preferably 5% by mass or less, more preferably 3% by mass or less, still more preferably 1% by mass or less, yet still more preferably 0.8% by mass or less, even yet still more preferably 0.5% by mass or less, and even still more preferably 0.3% by mass or less.

Cationic Polymer (B)

The hair cosmetic of the present invention contains a cationic polymer as the component (B). The component (B) has an action such that it makes the touch of the hair during applying the hair cosmetic or after applying the hair cosmetic and drying favorable and reduces damage of the hair. In addition, the component (B) suppresses a polymerization reaction of the component (A) outside the hair owing to an electrostatic action with the component (A), and therefore, it also has an action to improve the hair dyeing properties.

In the present invention, the cationic polymer refers to a water-soluble polymer having a cation group or a group capable of becoming a cation group through ionization (the foregoing groups will be also hereinafter referred to collectively as "cationic group"). However, the component (B) is a polymer having a cationic group but not having an anionic group.

The aforementioned anionic group refers to an anion group or a group capable of becoming an anion group through ionization.

Examples of the cationic polymer include a cationized guar gum; a cationized tam gum; a cationized locust bean gum; a cationized polyvinyl alcohol; a cationized cellulose; a cationized hydroxyalkyl cellulose, such as a cationized hydroxyethyl cellulose and a cationized hydroxypropyl cellulose; a cationic starch; a vinylpyrrolidone/N,N-dimethylaminoethyl methacrylate diethyl sulfate copolymer; a N,N-dimethylaminoethyl methacrylate diethyl sulfate/N,N-dimethyl acrylamide/dimethacrylic acid polyethylene glycol copolymer; polydiallyldimethylammonium chloride; a diallyldimethylammonium chloride/acrylamide copolymer; a hydroxyethyl cellulose/diallyldimethylammonium chloride copolymer; a vinyl imidazolium trichloride/vinylpyrrolidone copolymer; a vinylpyrrolidone/alkylamino (meth)acrylate copolymer; a vinylpyrrolidone/alkylamino (meth)acrylate/vinyl caprolactam copolymer; a vinylpyrrolidone/(meth)acrylamidopropyl trimethylammonium chloride copolymer; an alkyl acrylamide/(meth)acrylate/alkylaminoalkyl acrylamide/polyethylene glycol (meth)acrylate copolymer; and cationic polymers described in JP 53-139734 A and JP 60-36407 A. These can be used alone or in combination of two or more thereof.

Among those as mentioned above, from the viewpoint of making the touch of the hair favorable and the viewpoint of improving the hair dyeing properties, one or more selected from the group consisting of a cationized guar gum, a cationized tara gum, a cationized locust bean gum, a cationized polyvinyl alcohol, a cationized hydroxyalkyl cellulose, a vinylpyrrolidone/N,N-dimethylaminoethyl methacrylate diethyl sulfate copolymer, a N,N-dimethylaminoethyl methacrylate diethyl sulfate/N,N-dimethyl acrylamide/dimethacrylic acid polyethylene glycol copolymer, polydiallyldimethylammonium chloride, a diallyldimethylammonium chloride/acrylamide copolymer, and a vinyl imidazolium trichloride/vinylpyrrolidone copolymer are preferred; and one or more selected from the group consisting of a cationized guar gum, a cationized tara gum, a cationized locust bean gum, a cationized hydroxyalkyl cellulose, and a diallyldimethylammonium chloride/acrylamide copolymer are more preferred. Above all, one or more selected from the group consisting of a cationized guar gum and a cationized tara gum are still more preferred. In addition, from the viewpoint of suppressing the generation of precipitation to be caused owing to complex formation with the component (A), ones not having a structural unit derived from a diallyl quaternary ammonium salt are preferred.

In the present invention, among those as mentioned above, one or more cationic polymers can be used as the component (B).

From the viewpoint of suppressing the generation of precipitation to be caused owing to complex formation with the component (A) and the viewpoint of improving the dyeing properties, a cation charge density of the component (B) is preferably 0.05 meq/g or more, more preferably 0.1 meq/g or more, still more preferably 0.2 meq/g or more, and yet still more preferably 0.4 meq/g or more, and it is preferably 3.5 meq/g or less, more preferably 2.5 meq/g or less, still more preferably 2.0 meq/g or less, and yet still more preferably 1.5 meq/g or less.

The cation charge density of the component (B) refers to [(molar number of the cationic group contained per 1 gram of the cationic polymer)×1,000 (meq/g)].

Two or more cationic polymers may be used as the component (B). In this case, the cation charge density of the cationic polymer is determined through calculation by weighted averaging of cation charge densities and blending amounts of the respective cationic polymers.

Specifically, the cation charge density of the component (B) can be determined by a method described in the section of Examples.

Examples of a commercially available cationic polymer which can be used alone or in combination of two or more thereof as the component (B) include those described below.

Cationized Guar Gum

JAGUAR EXCEL (manufactured by Solvay (Novecare)), etc.

Cationized Tara Gum

CATINAL CTR-100 (manufactured by Toho Chemical Industry Co., Ltd.), etc.

Cationized Locust Bean Gum

CATINAL CLB-100 (manufactured by Toho Chemical Industry Co., Ltd.), etc.

Cationized Hydroxyethyl Cellulose

Polyquaternium-10 (o-[2-hydroxy-3-(trimethylammonio) propyl]hydroxyethyl cellulose chloride): for example, UCARE POLYMER JR-400 (manufactured by The Dow chemical Company), POISE C-60H (manufactured by Kao Corporation), POISE C-150L (manufactured by Kao Corporation), and CATICELO M-80 (manufactured by Kao Corporation)

Cationized Hydroxypropyl Cellulose

SOFCARE C-HP2 (manufactured by Kao Corporation), etc.

Cationized Polyvinyl Alcohol

GOHSENX K-434 (manufactured by The Nippon Synthetic Chemical Industry Co., Ltd.), CM318 (manufactured by Kuraray Co., Ltd.), etc.

Vinylpyrrolidone/N,N-dimethylaminoethyl methacrylate diethyl sulfate copolymer)

Polyquaternium-11: for example, GAFQUAT 734 (manufactured by ISP Japan Ltd.), GAFQUAT 755N (manufactured by ISP Japan Ltd.), etc.

N,N-Dimethylaminoethyl methacrylate diethyl sulfate/N,N-dimethyl acrylamide/dimethacrylic acid polyethylene glycol copolymer)

Polyquaternium -52: for example, SOFCARE KG-101W-E (manufactured by Kao Corporation), etc.

Polydiallyldimethylammonium Chloride

Polyquaternium-6: for example, MERQUAT 100 (manufactured by Lubrizol Advanced Materials), etc.

Diallyldimethylammonium chloride/acrylamide copolymer

Polyquaternium-7: for example, MERQUAT 550 (manufactured by Lubrizol Advanced Materials), etc.

Vinyl imidazolium trichloride/vinylpyrrolidone copolymer)

Polyquaternium-16: for example, LUVIQUAT FC370 (manufactured by BASF SE), etc.

From the viewpoint of making the touch of the hair favorable and the viewpoint of improving the hair dyeing properties, the content of the component (B) in the hair cosmetic is preferably 0.05% by mass or more, more preferably 0.1% by mass or more, still more preferably 0.15% by mass or more, yet still more preferably 0.2% by mass or more, even yet still more preferably 0.25% by mass or more, and even still more preferably 0.3% by mass or more. In addition, from the viewpoint of making the touch of the hair after rinsing and after drying favorable, the foregoing content is preferably 10% by mass or less, more preferably 5% by mass or less, still more preferably 3% by mass or less, yet still more preferably 1% by mass or less, and even yet still more preferably 0.6% by mass or less.

Component (C)

The hair cosmetic of the present invention contains, as the component (C), an ampholytic polymer having at least one cationic structural unit selected from the group consisting of a structural unit represented by the following general formula (2) and a structural unit represented by the following general formula (3), and an anionic structural unit. The component (C) has an action of suppressing the generation of precipitation to be caused owing to complex formation between the component (A) and the component (B) in the hair cosmetic, thereby making the appearance and the storage stability favorable.

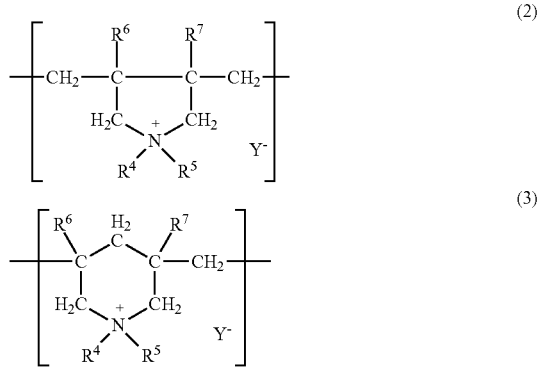

In the formulae, $R^4$ and $R^5$ each independently represent a hydrogen atom, an alkyl group having 1 or more and 18 or less carbon atoms, an aryl group, a hydroxyalkyl group, an amidoalkyl group, a cyanoalkyl group, an alkoxyalkyl group, or a carboalkoxyalkyl group; $R^6$ and $R^7$ each independently represent a hydrogen atom, an alkyl group having 1 or more and 3 or less carbon atoms, or a phenyl group; and $Y^-$ represents an anion, The structural unit represented by the general formula (2) and the structural unit represented by the general formula (3) are each a cationic structural unit derived from a diallyl quaternary ammonium salt.

In the general formula (2) and the general formula (3), from the viewpoint of making the storage stability favorable, $R^4$ and $R^5$ are each preferably an alkyl group having 1 or more and 18 or less carbon atoms, more preferably an alkyl group having 1 or more and 6 or less carbon atoms, still more preferably an alkyl group having 1 or more and 3 or less carbon atoms, and yet still more preferably a methyl group. From the viewpoint of making the storage stability favorable, $R^6$ and $R^7$ are each preferably a hydrogen atom or an alkyl group having 1 or more and 3 or less carbon atoms, and more preferably a hydrogen atom. In addition, examples of $Y^-$ include a chloride ion, a bromide ion, an iodide ion, a sulfate anion, a sulfonate anion, a methyl sulfate anion, a phosphate anion, and a nitrate anion.

The anionic structural unit which the component (C) has is not particularly limited so long as it is a structural unit derived from a monomer having an anionic group. Examples of the anionic group which the anionic structural unit has include a carboxy group, a sulfonate group, and a phosphate group. Of these, from the viewpoint of obtaining the effects of the present invention, the anionic structural unit is preferably a structural unit having a carboxy group.

Examples of the structural unit having a carboxy group include structural units derived from (meth)acrylic acid, crotonic acid, styrenecarboxylic acid, a maleic acid-based monomer, itaconic acid, or a salt thereof. Of these, from the viewpoint of easiness of availability, a structural unit derived from at least one selected from the group consisting of (meth)acrylic acid or a salt thereof, and styrenecarboxylic acid or a salt thereof is preferred, a structural unit derived from (meth)acrylic acid or a salt thereof is more preferred, and a structural nit derived from acrylic acid is still more preferred. The structural unit having a carboxy group may be alone or in combination of two or more thereof.

The (meth)acrylic acid refers to acrylic acid, methacrylic acid, or a mixture thereof; and the maleic acid-based monomer refers to maleic anhydride, maleic acid, a maleic acid monoester, or a maleic acid monoamide, or a mixture of two or more thereof.

The component (C) may have other structural unit than the aforementioned cationic structural unit and anionic structural unit. Examples of the foregoing structural unit include structural units derived from acrylamide, an alkyl (meth)acrylate, a (poly)alkylene glycol (meth)acrylate, or the like, with a structural unit derived from acrylamide being preferred. The foregoing structural unit may be alone or in combination of two or more thereof.

From the viewpoint of suppressing the generation of precipitation to be caused owing to complex formation between the component (A) and the component (B) and improving the dyeing properties, the content of the structural unit represented by the general formula (2) and the structural unit represented by the general formula (3) in the whole of structural units constituting the ampholytic polymer as the component (C) is more than 0 mol %, preferably 5 mol % or more, more preferably 10 mol % or more, still more preferably 15 mol % or more, yet still more preferably 20 mol % or more, and even yet still more preferably 25 mol % or more, and it is preferably 95 mol % or less, more preferably 90 mol % or less, still more preferably 85 mol % or less, and yet still more preferably 80 mol % or less.

From the viewpoint of suppressing the generation of precipitation to be caused owing to complex formation between the component (A) and the component (B), the content of the structural unit having an anionic group in the whole of structural units constituting the ampholytic polymer as the component (C) is more than 0 mol %, preferably 5 mol % or more, more preferably 10 mol % or more, still more preferably 15 mol % or more, yet still more preferably 20 mol % or more, and even yet still more preferably 25 mol % or more, and from the viewpoint of improvement in hair dyeing properties, it is preferably 95 mol % or less, more preferably 90 mol % or less, still more preferably 85 mol % or less, and yet still more preferably 80 mol % or less.

From the viewpoint of suppressing the generation of precipitation to be caused owing to complex formation between the component (A) and the component (B) and the viewpoint of improving the hair dyeing properties, the content of the other structural unit than the aforementioned cationic structural unit and anionic structural unit in the whole of structural units constituting the ampholytic polymer as the component (C) is preferably 70 mol % or less, more preferably 60 mol % or less, and still more preferably 50 mol % or less, and a lower limit thereof is 0 mol %.

From the viewpoint of suppressing the generation of precipitation to be caused owing to complex formation between the component (A) and the component (B) and the viewpoint of improving the hair dyeing properties, the component (C) is still more preferably an ampholytic polymer represented by the following general formula (4).

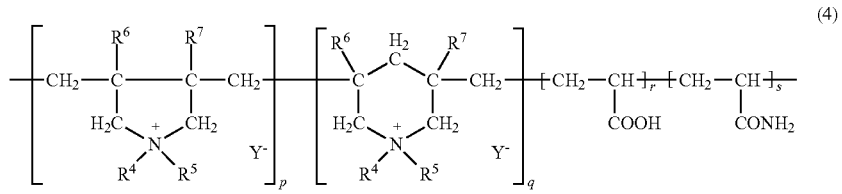

(4)

In the formula, $R^4$, $R^5$, $R^6$, $R^7$, and $Y^-$ are the same as mentioned above; p, q, r, and s each represent a molar fraction; and (p+q+r+s) is 100, provided that (p+q) is more than 0, and r is more than 0.

The ampholytic polymer represented by the general formula (4) is preferably at least one selected from the group consisting of a diallyldimethylammonium chloride/acrylic acid copolymer and a diallyldimethylammonium chloride/acrylic acid/acrylamide copolymer. That is, in the general formula (4), it is preferred that $R^4$ and $R^5$ are each a methyl group; $R^6$ and $R^7$ are each a hydrogen atom; and $Y^-$ is a chloride ion.

In the general formula (4), (p+q) is more than 0; and from the viewpoint of suppressing the generation of precipitation to be caused owing to complex formation between the component (A) and the component (B) and the viewpoint of improving the hair dyeing properties, (p+q) is preferably 5 or more, more preferably 10 or more, still more preferably 15 or more, yet still more preferably 20 or more, and even yet still more preferably 25 or more, and it is preferably 95 or less, more preferably 90 or less, still more preferably 85 or less, and yet still more preferably 80 or less.

In the general formula (4), r is more than 0; and from the viewpoint of suppressing the generation of precipitation to be caused owing to complex formation between the component (A) and the component (B), r is preferably 5 or more, more preferably 10 or more, still more preferably 15 or more, yet still more preferably 20 or more, and even yet still more preferably 25 or more, and from the viewpoint of improvement in hair dyeing properties, r is preferably 95 or less, more preferably 90 or less, still more preferably 85 or less, and yet still more preferably 80 or less.

In the general formula (4), from the viewpoint of suppressing the generation of precipitation to be caused owing to complex formation between the component (A) and the component (B) and the viewpoint of improving the hair dyeing properties, s is preferably 70 or less, more preferably 60 or less, and still more preferably 50 or less, and a lower limit thereof is 0.

In the general formula (4), a preferred combination of p, q, r, and s is one in which (p+q) is 5 or more and 95 or less, r is 5 or more and 95 or less, and s is 0 or more and 70 or less.

Examples of a commercially available ampholytic polymer which can be used alone or in combination of two or more thereof as the component (C) include those described below.

Diallyldimethylammonium chloride/acrylic acid copolymer)

Polyquaternium-22: MERQUAT 280 and MERQUAT 295 (all of which are manufactured by Lubrizol Advanced Materials), etc.

Diallyldimethylammonium chloride/acrylic acid/acrylamide polymer)

Polyquaternium-39: MERQUAT 3331PR and MERQUAT 3940 (all of which are manufactured by Lubrizol Advanced Materials), etc.

From the viewpoint of suppressing the generation of precipitation to be caused owing to complex formation between the component (A) and the component (B) and the viewpoint of improving the hair dyeing properties, the content of the component (C) in the hair cosmetic is preferably 0.035% by mass or more, more preferably 0.05% by mass or more, still more preferably 0.1% by mass or more, yet still more preferably 0.15% by mass or more, and even yet still more preferably 0.20% by mass or more. In addition, from the viewpoint of making the touch of the hair after rinsing and after drying favorable, the foregoing content is preferably 10% by mass or less, more preferably 5% by mass or less, still more preferably 3.5% by mass or less, yet still more preferably 3% by mass or less, and even yet still more preferably 1% by mass or less.

From the viewpoint of suppressing the generation of precipitation to be caused owing to complex formation between the component (A) and the component (B) and the viewpoint of improving the hair dyeing properties, a mass ratio of the component (C) to the component (A) [(C)/(A)] in the hair cosmetic is 0.7 or more and 10 or less. When the mass ratio (C)/(A) is 0.7 or more, the effect for suppressing the generation of precipitation and the effect for improving the hair dyeing properties are favorable. In addition, when the mass ratio (C)/(A) is 10 or less, the touch of the hair after rinsing and after drying is favorable.

From the aforementioned viewpoint, the mass ratio (C)/(A) of the component (C) to the component (A) in the hair cosmetic is preferably 0.9 or more, and more preferably 1.1 or more, and it is preferably 5.0 or less, more preferably 3.0 or less, and still more preferably 2.0 or less.

Anionic Surfactant (D)

It is preferred that the hair cosmetic of the present invention contains a component (D) that is an anionic surfactant. The component (D) gives a cleansing effect of the hair in the case where the hair cosmetic is a hair cleansing agent. In addition, the component (D) has an action of producing coacervation in a system in which the hair cosmetic is diluted with water through a combination with the cationic polymer as the component (B), whereby the component (A) is not only included in a high concentration within the coacervation but also adsorbed onto the hair surface, to reveal high hair dyeing properties.

Examples of the anionic surfactant include an alkylbenzene sulfonate, an alkyl or alkenyl ether sulfate, an alkyl or alkenyl sulfate, an olefin sulfonate, an alkane sulfonate, a saturated or unsaturated fatty acid salt, an alkyl or alkenyl ether carboxylate, an α-sulfo fatty acid salt, a N-acylamino acid, a phosphoric acid mono- or diester, and a sulfosuccinic acid ester. One or more of these anionic surfactants can be used.

Examples of a counter ion of an anionic group of the anionic surfactant include an alkali metal ion, such as a sodium ion and a potassium ion; an alkaline earth metal ion, such as a calcium ion and a magnesium ion; an ammonium ion; and an alkanolamine having 1 to 3 alkanol groups having 2 or 3 carbon atoms (for example, monoethanolamine, diethanolamine, triethanolamine, and triisopropanolamine).

Above all, from the viewpoint of favorable lathering, easiness for washing, and an improving effect for hair dyeing properties owing to coacervation formation in the case where the hair cosmetic is a hair cleansing agent, the component (D) is preferably one or more selected from the group consisting of an alkyl ether sulfate and an alkyl ether carboxylate. Examples of the alkyl ether sulfate include a polyoxyethylene alkyl ether sulfate, and examples of the alkyl ether carboxylate include a polyoxyethylene alkyl ether acetate.

From the viewpoint of favorable lathering, easiness for washing, and coacervation formation in the case where the hair cosmetic is a hair cleansing agent, the content of the component (D) in the hair cosmetic is preferably 3% by mass or more, more preferably 5% by mass or more, and still more preferably 8% by mass or more. In addition, from the viewpoint of improvement in hair dyeing properties and suppression of any damage to the hair, it is preferably 40% by mass or less, more preferably 30% by mass or less, still more preferably 20% by mass or less, and yet still more preferably 15% by mass or less.

Ampholytic Surfactant

The hair cosmetic of the present invention may further contain an ampholytic surfactant.

Examples of the ampholytic surfactant include a betaine-based surfactant, such as an alkyl dimethyl amino acetic acid betaine, a fatty acid amide propyl betaine, and an alkylhydroxy sulfobetaine; and a sultaine-based surfactant, such as lauryl hydroxysultaine. Above all, from the viewpoint of adaptability to hair and favorable lathering, a betaine-based surfactant is preferred, and a fatty acid amide propyl betaine is more preferred. The fatty acid amide propyl betaine is preferably one having an acyl group having 8 or more and 18 or less carbon atoms, and more preferably 10 or more and 16 or less carbon atoms, and one or more selected from the group consisting of lauric acid amide propyl betaine, a palm kernel oil fatty acid amide propyl betaine, and a coconut oil fatty acid amide propyl betaine are preferred.

In the case of using an ampholytic surfactant, from the viewpoint of adaptability to hair and favorable lathering, the content thereof in the hair cosmetic is preferably 0.05% by mass or more, more preferably 0.10% by mass or more, still more preferably 0.15% by mass or more, yet still more preferably 0.50% by mass or more, and even yet still more preferably 1.0% by mass or more, and it is preferably 15% by mass or less, more preferably 12% by mass or less, and still more preferably 10% by mass or less.

Cationic Surfactant

The hair cosmetic of the present invention may further contain a cationic surfactant.

Examples of the cationic surfactant include a mono- or di-long chain alkyl quaternary ammonium salt represented by the following general formula.

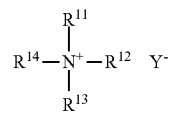

In the formula, $R^{11}$ represents a linear or branched alkyl group having 8 or more and 22 or less carbon atoms, or a group represented by $R^{15}CONH(CH_2)_m-$ or $R^{15}COO(CH_2)_m-$ ($R^{15}$ represents a linear or branched alkyl group having 7 or more and 21 or less carbon atoms, and m represents a number of 1 or more and 4 or less); $R^{12}$ represents a linear or branched alkyl group having 1 or more and 22 or less carbon atoms, or a group represented by the foregoing $R^{15}CONH(CH_2)_m-$ or $R^{15}COO(CH_2)_m-$; $R^{13}$ and $R^{14}$ each independently represent an alkyl group having 1 or more and 4 or less carbon atoms; and $Y^-$ represents a chloride ion, a bromide ion, or a methosulfate ion.

As specific examples of the cationic surfactant, from the viewpoint of imparting an excellent touch to the hair, one or more selected from the group consisting of a monoalkyltrimethylammonium chloride, a dialkyldimethylammonium chloride, and a monoalkyltrimethylammonium bromide are preferred. Above all, one or more selected from the group consisting of stearyltrimethylammonium chloride (steartrimonium chloride), cetyltrimethylammonium chloride (cetrimonium chloride), and lauryltrimethylammonium chloride (lauryltrimonium chloride) are more preferred.

In the case where the hair cosmetic contains a cationic surfactant, from the viewpoint of imparting an excellent touch to the hair, the content thereof in the hair cosmetic is preferably 0.01% by mass or more, and more preferably 0.05% by mass or more, and from the viewpoint of suppressing a lowering of touch of the hair, the foregoing content is preferably 10% by mass or less, and more preferably 5% by mass or less.

Nonionic Surfactant

The hair cosmetic of the present invention may further contain a nonionic surfactant.

Examples of the nonionic surfactant include a polyoxyalkylene alkyl ether, a polyoxyalkylene alkenyl ether, a polyoxyalkylene fatty acid ester, a higher fatty acid sucrose ester, a polyglycerin fatty acid ester, a polyoxyethylene hydrogenated castor oil, a polyoxyethylene sorbitan fatty acid ester, a polyoxyethylene sorbitol fatty acid ester, an alkyl saccharide, an alkylamine oxide, and an alkylamidoamine oxide. Of these, one or more selected from the group consisting of a polyoxyalkylene alkyl ether, a polyoxyethylene hydrogenated castor oil, and an alkyl saccharide are preferred, and a polyoxyalkylene alkyl ether is more preferred.

In the case where the hair cosmetic contains a nonionic surfactant, the content thereof in the hair cosmetic is preferably 0.01% by mass or more, and more preferably 0.02% by mass or more, and from the viewpoint of suppressing a lowering of touch of the hair, the foregoing content is preferably 5% by mass or less, and more preferably 3% by mass or less.

Alkaline Agent

It is preferred that the hair cosmetic of the present invention contains an alkaline agent. The alkaline agent has not only an action to swell the hair, thereby opening the cuticle and penetrating a dyeing agent component, such as the component (A), into the interior of the hair, but also an action to promote a polymerization reaction of the component (A), thereby improving the hair dyeing properties. As the alkaline agent, any material can be used without particular limitations so long as it is an alkaline agent that is used for usual hair dyes.

Examples of the alkaline agent include ammonia; alkanolamines, such as mono-, di-, or tri-methanolamine and mono-, di-, or tri-ethanolamine; alkylamines, such as methylamine, dimethylamine, ethylamine, diethylamine, N-methylethylamine, propylamine, and butylamine; aralkylamines, such as benzylamine; and inorganic alkaline compounds, such as sodium hydroxide and potassium hydroxide, and one or more of these materials can be used. From the viewpoint of water solubility, the carbon number of the alkanolamine, alkylamine, or aralkylamine is preferably 10 or less, and more preferably 8 or less.

Above all, from the viewpoint of hair dyeing properties, the alkaline agent is preferably one or more selected from the group consisting of ammonia, an alkanolamine, an alkylamine, an aralkylamine, sodium hydroxide, and potassium hydroxide. The hair cosmetic of the present invention more preferably contains one or more of ammonia and an alkanolamine, still more preferably contains a monoalkanolamine, and yet still more preferably contains monoethanolamine.

From the viewpoint of obtaining high hair dyeing properties, the content of the alkaline agent in the hair cosmetic is preferably 0.01% by mass or more, more preferably 0.1% by mass or more, and still more preferably 0.5% by mass or more, and from the viewpoint of suppressing irritation, it is preferably 10% by mass or less, more preferably 5% by mass or less, and still more preferably 3% by mass or less.

pH

From the viewpoint of promoting a polymerization reaction of the component (A) and improving the hair dyeing properties, a pH of the hair cosmetic of the present invention is preferably 8.0 or more, more preferably 8.5 or more, and still more preferably 9.0 or more. This is because the component (A) that is the melanin precursor reacts with oxygen in air under a basic condition, whereby it is liable to be converted into a melanin pigment. From the viewpoint of improving the hair dyeing properties and suppressing any damage to the hair, the foregoing pH is preferably 12.0 or less, more preferably 11.0 or less, still more preferably 10.5 or less, and yet still more preferably 10.0 or less.

The aforementioned pH is a measured value at 25° C., and specifically, it can be measured by a method described in the section of Examples.

Buffering Agent

It is preferred that the hair cosmetic of the present invention contains a buffering agent. In view of the fact of containing the buffering agent, for example, even in the case where the hair cosmetic is diluted with water during use, in order that the component (A) may reveal high hair dyeing properties, it is easy to maintain an optimum pH range.

Although the buffering agent is not particularly limited so long as it has a pH buffering action, since the component (A) that is the melanin precursor reacts with oxygen in air under a basic condition, whereby it is liable to be converted into a melanin pigment, a buffering agent capable of regulating the pH of the hair cosmetic to the basic condition is preferred.

From the aforementioned viewpoint, as for the buffering agent, a buffering agent containing, as a basic component, any one of a carbonate, such as sodium carbonate, potassium carbonate, sodium bicarbonate, and potassium bicarbonate, glycine, sodium tetraborate, and ammonium chloride, or a buffering agent composed of a combination of two or more basic components, such as sodium carbonate-sodium bicarbonate, is preferred; a buffering agent containing a carbonate is more preferred; and a buffering agent containing sodium bicarbonate is still more preferred.

From the viewpoint of improving the pH buffering ability, the buffering agent may further contain a protonating agent as a buffering agent component. The protonating agent may be any of a monobasic acid and a polybasic acid, and may be any of an organic acid (e.g., one having 1 or more and 8 or less carbon atoms, provided that ascorbic acid is excluded) and an inorganic acid. As the protonating agent, one or more selected from the group consisting of hydrochloric acid, sulfuric acid, phosphoric acid, formic acid, acetic acid, and citric acid are exemplified, and one or two selected from the group consisting of phosphoric acid and citric acid are more preferred.

From the viewpoint of improvement in hair dyeing properties, the buffering agent component constituting the buffering agent is still more preferably composed of a combination of sodium bicarbonate with one or two selected from the group consisting of phosphoric acid and citric acid.

Although the content of the buffering agent in the hair cosmetic is not particularly limited so long as it is an amount at which the pH of the hair cosmetic can be regulated to a desired range, it is preferably 0.5% by mass or more, more preferably 1.0% by mass or more, and still more preferably 1.5% by mass or more from the viewpoint of improving the pH buffering ability in the case where the hair cosmetic is diluted with water. In addition, from the viewpoint of formulation stability, the content of the buffering agent in the hair cosmetic is preferably 5.0% by mass or less, more preferably 4.0% by mass or less, and still more preferably 3.0% by mass or less.

The content of the buffering agent means a total amount of the active components of the buffering agent components constituting the buffering agent.

Other Components

The hair cosmetic of the present invention may appropriately contain, in addition to the aforementioned components, a component which is usually used for hair cosmetics or hair dyes, within a range where the purpose of the present invention is not impaired. Examples of the foregoing component include an antioxidant, a silicone, an aromatic alcohol, a dyeing agent other than the component (A), an aqueous medium, a polymer other than the components (B) and (C), an oil, an anti-dandruff agent, a vitamin compound, a disinfectant, an antiinflammatory agent, an antiseptic, a chelating agent, a humectant, a pearlescent agent, a ceramide, a perfume, and an ultraviolet absorber.

Antioxidant

Examples of the antioxidant include sulfurous acid, ascorbic acid, thioglycolic acid, L-cysteine, and N-acetyl-L-cysteine, and salts thereof. From the viewpoint of stabilization of the component (A) and improvement in dyeing properties, ascorbic acid and a salt thereof are preferred.

In the case of using the antioxidant, the content thereof in the hair cosmetic is preferably 0.05% by mass or more, and more preferably 0.1% by mass or more, and it is preferably 10% by mass or less, more preferably 5% by mass or less, and still more preferably 2% by mass or less.

Silicone

For example, in the case where the hair cosmetic is a hair cleansing agent, the silicone has an effect for improving foam texture, foam slipperiness, crease reduction during cleansing, and smoothness during drying. Examples of the silicone include dimethyl polysiloxane; methylphenyl polysiloxane; an amino-modified silicone, such as amodimethicone, aminoethylaminopropyl dimethicone, and aminopropyl dimethicone a cyclic silicone; a polyether-modified silicone; a fatty acid-modified silicone; an alcohol-modified silicone; an alkoxy-modified silicone; an epoxy-modified silicone; a fluorine-modified silicone; and an alkyl-modified silicone. One or more of these silicones can be contained.

Above all, dimethyl polysiloxane is preferred as the silicone from the viewpoint of improving foam texture, foam slipperiness, crease reduction during cleansing, and smoothness during drying.

In the case of using the silicone, the content thereof in the hair cosmetic is preferably 0.1% by mass or more, more preferably 0.2% by mass or more, still more preferably 0.5% by mass or more, and yet still more preferably 2% by mass or more from the viewpoint of improving foam texture, foam slipperiness, crease reduction during cleansing, and smoothness during drying, and it is preferably 15% by mass or less, more preferably 10% by mass or less, and still more preferably 8% by mass or less from the viewpoint of improving foam texture, foam slipperiness, crease reduction during cleansing, and smoothness during drying and the viewpoint of economy.

Aromatic Alcohol

From the viewpoint of solubility of the component (B), the hair cosmetic of the present invention may further contain an aromatic alcohol. Examples of the aromatic alcohol include benzyloxyethanol, benzyl alcohol, phenethyl alcohol, γ-phenylpropyl alcohol, cinnamic alcohol, anise alcohol, p-methylbenzyl alcohol, α,α-dimethylphenethyl alcohol, α-phenyl ethanol, and phenoxyethanol. Of these, one or more selected from the group consisting of benzyloxyethanol and benzyl alcohol are preferred, and benzyl alcohol is more preferred.

In the case of using the aromatic alcohol, from the viewpoint of solubility of the component (B), the content thereof in the hair cosmetic is preferably 0.05% by mass or more, and more preferably 0.1% by mass or more, and it is preferably 5% by mass or less, more preferably 3% by mass or less, and still more preferably 2% by mass or less.

Dyeing Agent Other Than Component (A)

The hair cosmetic of the present invention may further contain a dyeing agent other than the component (A). Examples of the foregoing dyeing agent include an oxidation dye (constituted of a precursor and a coupler) and a direct dye, each of which is typically used for hair dyes.

As the dying agent other than the component (A), one or more materials can be used. The foregoing dyeing agent is preferably an oxidation dye. As the precursor, paraphenylenediamine, toluene-2,5-diamine, paraaminophenol, 4-aminometacresol, 1-hydroxyethyl-4,5-diaminopyrazole, and salts thereof are preferred; and as the coupler, 2,4-diaminophenoxyethanol, metaaminophenol, 2-methyl-5-aminophenol, resorcin, 2-methylresorcin, 4-chlororesorcinol, 1-naphthol, 2-amino-3-hydroxypyridine, 2-amino-4-(β-hydroxyethyl)aminoanisole, and salts thereof are preferred.

In the case of using the dyeing agent other than the component (A), the content thereof in the hair cosmetic is preferably 0.01% by mass or more, and more preferably 0.05% by mass or more from the viewpoint of improvement in hair dyeing properties, and it is preferably 1% by mass or less, and more preferably 0.5% by mass or less from the viewpoint of obtaining a natural color shade through hair dyeing with the component (A).

Aqueous Medium

The hair cosmetic typically contains an aqueous medium. Examples of the aqueous medium include water; a lower alcohol, such as ethanol and isopropyl alcohol; and a low-molecular diol or triol having 6 or less carbon atoms, such as 1,3-butylene glycol, glycerin, ethylene glycol, and propylene glycol, with water being preferred. Although the content of the aqueous medium in the hair cosmetic can be appropriately selected depending upon the formulation of the hair cosmetic, it is typically in a range of 1 to 95% by mass. In the case of using water as the aqueous medium, from the viewpoint of easiness of applying the hair cosmetic on the hair and revealing high hair dyeing properties, the content of water in the hair cosmetic is preferably 50% by mass or more, more preferably 60% by mass or more, and still more preferably 70% by mass, and it is preferably 95% by mass or less, and more preferably 90% by mass or less.

A production method of the hair cosmetic of the present invention is not particularly limited. For example, the hair cosmetic of the present invention can be produced by blending the components (A) to (C), and other components which are used, if desired by a method described in the section of Examples and mixing the blend by using a known stirring device or the like.

Dyeing Method of Hair

The present invention further provides a dyeing method of hair including a step of applying the aforementioned hair cosmetic on hair. For example, in the case where the hair cosmetic is a hair cleansing agent, such as a shampoo, the hair cleansing agent is applied on hair, lathered to cleanse the hair, and then rinsed away with water. In the case where the hair cosmetic is a hair conditioning agent, a hair treatment agent, or a hair dye, the hair cosmetic is applied on hair, optionally allowed to stand for a short time (about 1 to 5 minutes), and then rinsed away with water. By daily repeating such a step, gray hair dyeing can be performed easily and within a short period of time.

Regarding the aforementioned embodiments, the present invention discloses the following hair cosmetics and dyeing methods of hair.

<1> A hair cosmetic containing the following components (A) to (C):

(A) 0.05% by mass or more and 3% by mass or less of a compound represented by the following general formula (1) or a salt thereof:

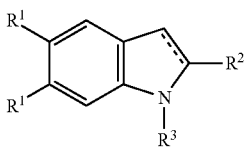

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) 0.1% by mass or more and 5% by mass or less of a cationic polymer; and (C) an ampholytic polymer having at least one cationic structural unit selected from the group consisting of a structural unit represented by the following general formula (2) and a structural unit represented by the following general formula (3), and an anionic structural unit:

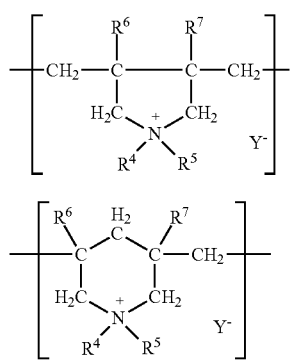

(2)

(3)

wherein $R^4$ and $R^5$ each independently represent a hydrogen atom, an alkyl group having 1 or more and 18 or less carbon atoms, an aryl group, a hydroxyalkyl group, an amidoalkyl group, a cyanoalkyl group, an alkoxyalkyl group, or a carboalkoxyalkyl group; $R^6$ and $R^7$ each independently represent a hydrogen atom, an alkyl group having 1 or more and 3 or less carbon atoms, or a phenyl group; and $Y^-$ represents an anion, a mass ratio of the component (C) to the component (A) [(C)/(A)] being 0.7 or more and 10 or less.

<2> A hair cosmetic containing the following components (A) to (C):

(A) 0.05% by mass or more and 3% by mass or less of a compound represented by the following general formula (1) or a salt thereof;

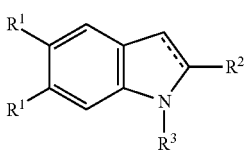

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) a cationic polymer; and (C) 0.1% by mass or more and 5% by mass or less of an ampholytic polymer having at least one cationic structural unit selected from the group consisting of a structural unit represented by the following general formula (2) and a structural unit represented by the following general formula (3), and an anionic structural unit:

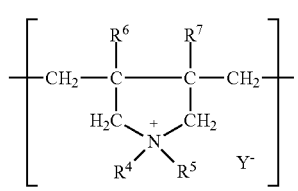

(2)

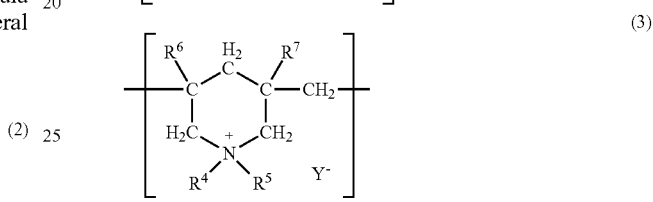

(3)

wherein $R^4$ and $R^5$ each independently represent a hydrogen atom, an alkyl group having 1 or more and 18 or less carbon atoms, an aryl group, a hydroxyalkyl group, an amidoalkyl group, a cyanoalkyl group, an alkoxyalkyl group, or a carboalkoxyalkyl group; $R^6$ and $R^7$ each independently represent a hydrogen atom, an alkyl group having 1 or more and 3 or less carbon atoms, or a phenyl group; and $Y^-$ represents an anion, a mass ratio of the component (C) to the component (A) [(C)/(A)] being 0.7 or more and 10 or less.

<3> A hair cosmetic containing the following components (A) to (C):

(A) a compound represented by the following general formula (1) or a salt thereof;

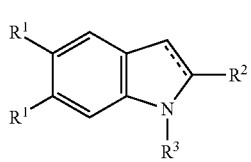

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) 0.05% by mass or more and 5% by mass or less of a cationic polymer; and (C) 0.1% by mass or more and 5% by mass or less of an ampholytic polymer having at least one cationic structural unit selected from the group consisting of a structural unit represented by the following general formula (2) and a structural unit represented by the following general formula (3), and an anionic structural unit:

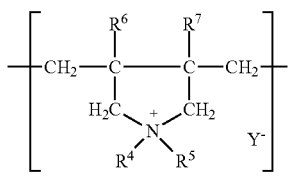

(2)

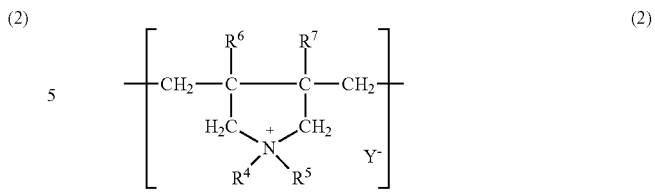

(2)

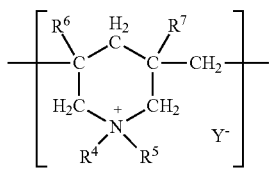

(3)

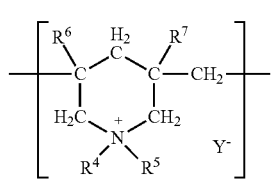

(3)

wherein $R^4$ and $R^5$ each independently represent a hydrogen atom, an alkyl group having 1 or more and 18 or less carbon atoms, an aryl group, a hydroxyalkyl group, an amidoalkyl group, a cyanoalkyl group, an alkoxyalkyl group, or a carboalkoxyalkyl group; $R^6$ and $R^7$ each independently represent a hydrogen atom, an alkyl group having 1 or more and 3 or less carbon atoms, or a phenyl group; and $Y^-$ represents an anion, a mass ratio of the component (C) to the component (A) [(C)/(A)] being 0.9 or more and 5.0 or less.

<4> A hair cosmetic containing the following components (A) to (C):

(A) 0.05% by mass or more and 0.8% by mass or less of a compound represented by the following general formula (1) or a salt thereof:

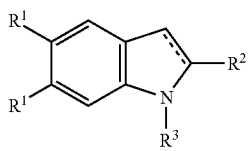

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) 0.05% by mass or more and 1% by mass or less of a cationic polymer; and (C) 0.1% by mass or more and 1% by mass or less of an ampholytic polymer having at least one cationic structural unit selected from the group consisting of a structural unit represented by the following general formula (2) and a structural unit represented by the following general formula (3), and an anionic structural unit:

wherein $R^4$ and $R^5$ each independently represent a hydrogen atom, an alkyl group having 1 or more and 18 or less carbon atoms, an aryl group, a hydroxyalkyl group, an amidoalkyl group, a cyanoalkyl group, an alkoxyalkyl group, or a carboalkoxyalkyl group; $R^6$ and $R^7$ each independently represent a hydrogen atom, an alkyl group having 1 or more and 3 or less carbon atoms, or a phenyl group; and $Y^-$ represents an anion, a mass ratio of the component (C) to the component (A) [(C)/(A)] being 0.7 or more and 3.0 or less.

<5> The hair cosmetic as set forth in any one of <1> to <4>, wherein a cation charge density of the component (B) is 0.2 to 3.5 meq/g.

<6> The hair cosmetic as set forth in any one of <1> to <5>, wherein the component (B) is at least one selected from the group consisting of a cationized guar gum, a cationized tara gum, a cationized locust bean gum, a cationized polyvinyl alcohol, a cationized hydroxyalkyl cellulose, a vinylpyrrolidone/N,N-dimethylaminoethyl methacrylate diethyl sulfate copolymer, a N,N-dimethylaminoethyl methacrylate diethyl sulfate/N,N-dimethyl acrylamide/dimethacrylic acid polyethylene glycol copolymer, polydiallyldimethylammonium chloride, a diallyldimethylammonium chloride/acrylamide copolymer, and a vinyl imidazolium trichloride/vinylpyrrolidone copolymer.

<7> The hair cosmetic as set forth in any one of <1> to <4>, wherein the component (B) is at least one selected from the group consisting of a cationized guar gum, a cationized tara gum, a cationized locust bean gum, a cationized hydroxyalkyl cellulose, and a diallyldimethylammonium chloride/acrylamide copolymer, each having a cation charge density of 0.2 to 3.5 meq/g.

<8> The hair cosmetic as set forth in any one of <1> to <5>, wherein the component (B) does not have a structural unit derived from a diallyl quaternary ammonium salt.

<9> The hair cosmetic as set forth in any one of <1> to <8>, wherein the anionic structural unit of the component (C) is a structural unit containing a carboxy group.

<10> The hair cosmetic as set forth in <9>, wherein the component (C) is an ampholytic polymer represented by the following general formula (4):

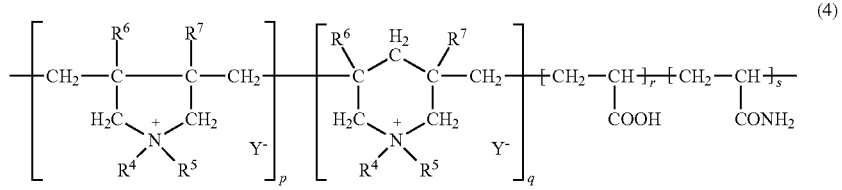

(4)

wherein $R^4$, $R^5$, $R^6$, $R^7$, and $Y^-$ are the same as mentioned above; p, q, r, and s each represent a molar fraction; and (p+q+r+s) is 100, provided that (p+q) is more than 0, and r is more than 0.

<11> The hair cosmetic as set forth in <10>, wherein in the general formula (4), (p+q) is 5 or more and 95 or less; r is 5 or more and 95 or less; and s is 0 or more and 70 or less.

<12> The hair cosmetic as set forth in any one of <1> to <11>, wherein the component (C) is at least one selected from the group consisting of a diallyldimethylammonium chloride/acrylic acid copolymer and a diallyldimethylammonium chloride/acrylic acid/acrylamide copolymer.

<13> The hair cosmetic as set forth in any one of <1> to <12>, wherein a pH is 8.0 or more and 12.0 or less.

<14> The hair cosmetic as set forth in any one of <1> to <13>, wherein a pH is 8.5 or more and 11.0 or less.

<15> The hair cosmetic as set forth in any one of <1> to <14>, wherein a pH is 9.0 or more and 10.0 or less.

<16> The hair cosmetic as set forth in any one of <1> to <15>, wherein the content of the component (A) is 0.1% by mass or more and 0.8% by mass or less.

<17> The hair cosmetic as set forth in any one of <1> to <16>, wherein the content of the component (A) is 0.1% by mass or more and 0.5% by mass or less.

<18> The hair cosmetic as set forth in any one of <1> to <17>, wherein the content of the component (A) is 0.1% by mass or more and 0.3% by mass or less.

<19> The hair cosmetic as set forth in any one of <1> to <18>, further containing (D) an anionic surfactant.

<20> The hair cosmetic as set forth in <19>, which is a hair cleansing agent.

<21> A dyeing method of hair including a step of applying the hair cosmetic as set forth in any one of <1> to <20> on hair.

EXAMPLES

The present invention is hereunder described by reference to Examples, but it should be construed that the present invention is not limited to the scope of the Examples. In the present Examples, the measurement of cation charge density, nitrogen content, and pH was performed by the following methods.

Measurement of Cation Charge Density

The cation charge density of a cationic polymer was calculated according to the following expression (1) unless other specifically mentioned.

Cation charge density (meq/g)=[Nitrogen content (% by mass)]÷14×10     (1)

In the expression (1), the nitrogen content (% by mass) was measured by the Kjeldahl method as mentioned below. In addition, in the case where nitrogen other than the nitrogen of the quaternary ammonium cation is contained in the polymer, the cation charge density was determined while defining a value obtained by multiplying the nitrogen content determined by the Kjeldahl method as mentioned below by a value of [(nitrogen number of quaternary ammonium cation)/(total nitrogen number)] as the nitrogen content in the expression (1).

Measurement Method of Nitrogen Content (% by mass) (Kjeldahl Method)

100 mg of a polymer which had been purified and dried, if desired was accurately metered, to which were then added 10 mL of sulfuric acid and one tablet of (5 g) of a decomposition accelerator ("Kjeldahl tablet", manufactured by Merck), and then, complete decomposition was performed with a Kjeldahl decomposition apparatus ("K-432", manufactured by BUCHI) while undergoing temperature rise at 250° C. for 30 minutes, at 300° C. for 30 minutes, and at 420° C. for 80 minutes in this order. After completion of decomposition reaction, 30 mL of ion-exchanged water was added to the sample. Using an automatic Kjeldahl distillation and titration apparatus ("K-370", manufactured by BUCHI), 40 mL of a 30% sodium hydroxide aqueous solution was added to make the sample alkaline, and then, ammonia liberated by means of a distillation operation was collected in a 1% boric acid aqueous solution, followed by titration with 0.01N sulfuric acid (for quantitative analysis, manufactured by Wako Pure Chemical Industries, Ltd.) to determine the nitrogen content (% by mass) in the polymer.

pH Measurement

A pH at 25° C. of the hair cosmetic was measured with a pH meter (F-51, manufactured by HORIBA, Ltd.).

Preparation of Hair Cosmetic

Examples 1 to 6 and Comparative Examples 1 to 5

According to the composition shown in Table 1, an anionic surfactant and a part of water were mixed to prepare an aqueous solution, and then, an ampholytic polymer, a cationic polymer dispersed in water, and benzyl alcohol were added and dissolved at 75° C. At this time, among the cationic polymers, each of a cationized guar gum and a cationized tara gum was added upon being dispersed in benzyl alcohol. After cooling, an alkaline agent, a buffering agent, and an ampholytic surfactant were added, and then, a solution of the component (A) was added in a nitrogen atmosphere, to prepare a hair cosmetic. All of the hair cosmetics had a pH of 9.6. Each of the prepared hair cosmetics was stored in a nitrogen atmosphere and aliquoted on each occasion of evaluation of hair dyeing properties, and the following evaluation was carried out.

Examples 7 to 19 and Comparative Examples 6 to 9

According to the composition shown in Table 2, an ampholytic polymer and benzyl alcohol were added to a part of water and dissolved at 75° C. The addition method of a cationic polymer was the same as mentioned above. After cooling, hair cosmetics were prepared in the same manner as mentioned above, except that the ampholytic surfactant was not added, and the following evaluation was carried out. All of the hair cosmetics had a pH of 9.6.

Stability Evaluation

The "stability" in the present invention means an effect for suppressing a deposit produced from the component (A) and the component (C). With respect to the stability, on the occasion of filling the hair cosmetic of each of the Examples in a 100-mL standard bottle and storing for a fixed period of time, the resulting hair cosmetic was evaluated in terms of an appearance. The appearance was visually observed after storing at 50° C. for 1 month with respect to the hair cosmetics of Examples 1 to 6 and Comparative Examples 1 to 5, each having the surfactant blended therein (see Table 1), and immediately after blending (see Table 2) with respect to the hair cosmetics of Examples 7 to 19 and Comparative Examples 6 to 9 each not having the surfactant blended therein, and the evaluation was made according to the following criteria.

A: A deposit is not perceived at all, and the resulting hair cosmetic is uniform and transparent.

B: A state where the resulting hair cosmetic is opaque, and a deposit is perceived but minute, and is uniformly dispersed.

C: A state where a deposit is perceived and aggregated, and it locally exists, or a precipitate is formed.

TABLE 1

| | | | Example | | | | | | Comparative Example | | | | |
|---|---|---|---|---|---|---|---|---|---|---|---|---|---|
| | | | 1 | 2 | 3 | 4 | 5 | 6 | 1 | 2 | 3 | 4 | 5 |
| (A) | Compound represented by the general formula (1) or its salt | (A1) 5,6-Dihydroxyindole solution *1 | 15.00 | 15.00 | 15.00 | 15.00 | 15.00 | 15.00 | 15.00 | 15.00 | 15.00 | 15.00 | 15.00 |
| (B) | Cationic polymer | Cationized guar gum *2 | 0.30 | 0.30 | 0.30 | | | | 0.30 | | | | 0.30 |
| | | Cationized tara gum *3 | | | | 0.30 | | | | 0.30 | | | |
| | | Cationized locust bean gum *4 | | | | | 0.30 | | | | 0.30 | | |
| | | Cationized hydroxypropyl cellulose *5 | | | | | | 0.30 | | | | 0.30 | |
| (C) | Ampholytic polymer | Polyquaternium-22 *6 | 0.20 | 0.30 | | 0.20 | 0.20 | 0.20 | | | | | |
| | | Polyquaternium-39 *7 | | | 0.20 | | | | | | | | |
| (C)' | Ampholytic polymer | Polyquaternium-53 *8 | | | | | | | | | | | 0.20 |
| Others | Anionic surfactant (27.0%) *9 | | 40.00 | 40.00 | 40.00 | 40.00 | 40.00 | 40.00 | 40.00 | 40.00 | 40.00 | 40.00 | 40.00 |
| | Ampholytic surfactant (28.8%) *10 | | 15.00 | 15.00 | 15.00 | 15.00 | 15.00 | 15.00 | 15.00 | 15.00 | 15.00 | 15.00 | 15.00 |
| | Benzyl alcohol | | 0.50 | 0.50 | 0.50 | 0.50 | 0.50 | 0.50 | 0.50 | 0.50 | 0.50 | 0.50 | 0.50 |
| | Ascorbic acid | | 0.20 | 0.20 | 0.20 | 0.20 | 0.20 | 0.20 | 0.20 | 0.20 | 0.20 | 0.20 | 0.20 |
| | Phosphoric acid (75%) *11 | | 0.30 | 0.30 | 0.30 | 0.30 | 0.30 | 0.30 | 0.30 | 0.30 | 0.30 | 0.30 | 0.30 |
| | Monoethanolamine | | 1.50 | 1.50 | 1.50 | 1.50 | 1.50 | 1.50 | 1.50 | 1.50 | 1.50 | 1.50 | 1.50 |
| | Sodium bicarbonate | | 2.00 | 2.00 | 2.00 | 2.00 | 2.00 | 2.00 | 2.00 | 2.00 | 2.00 | 2.00 | 2.00 |
| | Water | | 25.00 | 24.90 | 25.00 | 25.00 | 25.00 | 25.00 | 25.20 | 25.20 | 25.20 | 25.20 | 25.00 |
| | Total | | 100.0 | 100.0 | 100.0 | 100.0 | 100.0 | 100.0 | 100.0 | 100.0 | 100.0 | 100.0 | 100.0 |
| | (C)/(A) mass ratio | | 1.17 | 1.75 | 1.17 | 1.17 | 1.17 | 1.17 | — | — | — | — | — |
| | Stability (appearance evaluation) | | A | A | A | A | A | A | C | C | C | C | C |

TABLE 2

| | | Example | | Comparative Example | | | | Example | | | | | | | | | | | |
|---|---|---|---|---|---|---|---|---|---|---|---|---|---|---|---|---|---|---|---|
| | | 7 | 8 | 6 | 7 | 8 | 9 | 9 | 10 | 11 | 12 | 13 | 14 | 15 | 16 | 17 | 18 | 19 |
| (A) | Compound represented by general formula (1) or its salt | | | | | | | | | | | | | | | | | |
| | (A1) 5,6-Dihydroxyindole solution *1 | 15.00 | 15.00 | 15.00 | 15.00 | 15.00 | 15.00 | 15.00 | 15.00 | 15.00 | 15.00 | 15.00 | 15.00 | 15.00 | | | 15.00 | 15.00 |
| | (A2) 5,6-Dihydroxyindole solution *12 | | | | | | | | | | | | | | 15.00 | | | |
| | (A3) 5,6-Dihydroxyindoline·HBr solution *13 | | | | | | | | | | | | | | | 15.00 | | |
| (B) | Cationic polymer | | | | | | | | | | | | | | | | | |
| | Cationized guar gum *2 | 0.30 | | 0.30 | | 0.30 | 0.30 | 0.30 | 0.30 | 0.30 | | | 0.10 | 0.60 | 0.30 | 0.30 | 0.30 | 0.30 |
| | Cationized tara gum *3 | | 0.30 | | 0.30 | | | | | | | | | | | | | |
| | Cationized hydroxypropyl cellulose *5 | | | | | | | | | | | 0.30 | | | | | | |
| | Polyquaternium-7 *14 | | | | | | | | | | 0.30 | | | | | | | |
| (C) | Ampholytic polymer | | | | | | | | | | | | | | | | | |
| | Polyquaternium-22 *6 | 0.20 | 0.20 | | | | 0.10 | 0.15 | 0.30 | 0.50 | 0.20 | 0.20 | 0.20 | 0.20 | 0.20 | 0.20 | 0.20 | 0.20 |
| (C)' | Ampholytic polymer | | | | | | | | | | | | | | | | | |
| | Polyquaternium-53 *8 | | | | | 0.20 | | | | | | | | | | | | |
| Others | Benzyl alcohol | 0.50 | 0.50 | 0.50 | 0.50 | 0.50 | 0.50 | 0.50 | 0.50 | 0.50 | 0.50 | 0.50 | 0.50 | 0.50 | 0.50 | 0.50 | 0.50 | 0.50 |
| | Ascorbic acid | 0.20 | 0.20 | 0.20 | 0.20 | 0.20 | 0.20 | 0.20 | 0.20 | 0.20 | 0.20 | 0.20 | 0.20 | 0.20 | 0.20 | 0.20 | 0.20 | 0.20 |
| | Phosphoric acid (75%) *11 | 0.30 | 0.30 | 0.30 | 0.30 | 0.30 | 0.30 | 0.30 | 0.30 | 0.30 | 0.30 | 0.30 | 0.30 | 0.30 | 0.30 | 0.30 | 0.30 | 0.30 |
| | Monoethanolamine | 1.50 | 1.50 | 1.50 | 1.50 | 1.50 | 1.50 | 1.50 | 1.50 | 1.50 | 1.50 | 1.50 | 1.50 | 1.50 | 1.50 | 1.50 | 1.50 | 1.50 |
| | Sodium bicarbonate | 2.00 | 2.00 | 2.00 | 2.00 | 2.00 | 2.00 | 2.00 | 2.00 | 2.00 | 2.00 | 2.00 | 2.00 | 2.00 | 2.00 | 2.00 | 2.00 | 2.00 |
| | Oxidation dye X *15 | | | | | | | | | | | | | | | | 0.12 | |
| | Oxidation dye Y *16 | | | | | | | | | | | | | | | | | 0.10 |
| | Water | 80.00 | 80.00 | 80.20 | 80.20 | 80.00 | 80.10 | 80.05 | 79.90 | 79.70 | 80.00 | 80.00 | 80.20 | 79.70 | 80.00 | 80.00 | 79.88 | 79.90 |
| | Total | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 |
| | (C)/(A) mass ratio | 1.17 | 1.17 | — | — | — | 0.58 | 0.88 | 1.75 | 2.92 | 1.17 | 1.17 | 1.17 | 1.17 | 1.33 | 1.33 | 1.17 | 1.17 |
| | Stability (appearance evaluation) | A | A | C | C | C | C | A | A | A | A | A | A | A | A | A | A | A |

The components described in the tables are shown below. All of the blending amounts (% by mass) of the respective components described in the tables are tangible.

*1: (A1) 5,6-Dihydroxyindole solution; Solution produced by the method described in Japanese Patent No. 5570161 (5,6-dihydroxyindole: 1% by mass, 5,6-dihydroxyindole-2-carboxylic acid: 0.14% by mass, ethanol: 20% by mass, water: remainder)
*2: Cationized guar gum; JAGUAR EXCEL (manufactured by Solvay (Novecare), cation charge density=1.1 meq/g)
*3: Cationized tara gum; CATINAL CTR-100 (manufactured by Toho Chemical Industry Co., Ltd., cation charge density=1.3 meq/g)
*4: Cationized locust bean gum: CATINAL CLB-100 (manufactured by Toho Chemical Industry Co., Ltd., cation charge density=1.0 meq/g)
*5: Cationized hydroxypropyl cellulose; SOFCARE C-HP2 (manufactured by Kao Corporation, cation charge density=0.5 meq/g)
*6: Polyquaternium-22; Diallyldimethylammonium chloride/acrylic acid copolymer, MERQUAT 280 (manufactured by Lubrizol Advanced Materials; in the general formula (4), (p+q) is 65, r is 35, and s is 0)
*7: Polyquaternium-39; Diallyldimethylammonium chloride/acrylic acid/acrylamide copolymer, MERQUAT 3940 (manufactured by Lubrizol Advanced Materials; in the general formula (4), (p+q) is 29, r is 31, and s is 40)
*8: Polyquaternium-53; Methacrylamidopropyltrimonium chloride/acrylic acid/acrylamide copolymer (molar ratio: 40/10/50), MERQUAT 2003PR (manufactured by Lubrizol Advanced Materials)
*9: Anionic surfactant; Sodium polyoxyethylene lauryl ether sulfate, EMAL E-27C (manufactured by Kao Corporation, active component amount: 27.0% by mass)
*10: Ampholytic surfactant; Lauric acid amide propyl betaine, AMPHITOL 20AB (manufactured by Kao Corporation, active component amount: 28.8% by mass)
*11: Phosphoric acid; Food additive 75% phosphoric acid (manufactured by Nippon Chemical Industrial Co., Ltd.)
*12: (A2) 5,6-Dihydroxyindole solution (manufactured by Matrix Scientific, 5,6-dihydroxyindole: 1% by mass, ethanol: 20% by mass, water: remainder)
*13: (A3) 5,6-Dihydroxyindoline hydrobromide solution (manufactured by AK-scientific, 5,6-dihydroxyindoline hydrobromide: 1% by mass, ethanol: 20% by mass, water: remainder)
*14: Polyquaternium-7; MERQUAT 550 (manufactured by Lubrizol Advanced Materials, cation charge density=3.1 meq/g)
*15: Oxidation dye X; Toluene-2,5-diamine sulfate: 0.02% by mass, paraaminophenol: 0.02% by mass, metaaminophenol: 0.02% by mass, resorcin: 0.02% by mass, 2,4-diaminophenoxyethanol hydrochloride: 0.02% by mass, and 2-methyl-5-aminophenol: 0.02% by mass (all of the term "% by mass" mean the amount relative to the whole amount of the hair cosmetic)
*16: Oxidation dye Y; Paraphenylenediamine sulfate: 0.02% by mass, 4-aminometacresol: 0.02% by mass, 2-methylresorcin: 0.02% by mass, 2-amino-3-hydroxypyridine: 0.02% by mass, and 2-amino-4-(β-hydroxyethyl)aminoanisole sulfate: 0.02% by mass, (all of the term "% by mass" mean the amount relative to the whole amount of the hair cosmetic)

From Tables 1 and 2, it is noted that all of the hair cosmetics of the present Examples containing the predetermined ampholytic polymer (C) in a predetermined proportion are free from generation of precipitation and the like and excellent in the storage stability. In contrast, there were brought such results that all of the hair cosmetics of Comparative Examples 1 to 4, 6, and 7, each not containing the ampholytic polymer, Comparative Examples 5 and 8, each using other ampholytic polymer than the component (C), and Comparative Example 9 having the mass ratio (C)/(A) of less than 0.7 were inferior in the storage stability.

INDUSTRIAL APPLICABILITY

The hair cosmetic of the present invention is free from generation of precipitation to be caused owing to complex formation between a melanin precursor and a cationic polymer and favorable in storage stability and appearance. In addition, when the hair cosmetic of the present invention is used, it is possible to obscure gray hairs through a daily hair care behavior, such as shampooing and hair treatment.

The invention claimed is:
1. A hair cosmetic, comprising:
(A) a compound represented by the following formula (1) or a salt thereof:

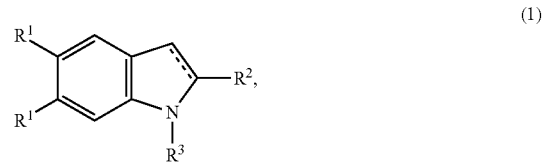

wherein a broken line represents the presence or absence of a π bond; $R^1$ represents a hydroxy group or an acetoxy group; $R^2$ represents a hydrogen atom or —COOR, wherein R is a hydrogen atom, a methyl group, or an ethyl group; and $R^3$ represents a hydrogen atom, an acetyl group, a methyl group, or an ethyl group;
(B) a cationic polymer does not comprise a structural unit derived from a diallyl quaternary ammonium salt and has a cation charge density of from 0.05 meq/g to 2.5 meq/g; and
(C) an ampholytic polymer having at least one cationic structural unit selected from the group consisting of a structural unit represented by the following formula (2) and a structural unit represented by the following formula (3), and an anionic structural unit:

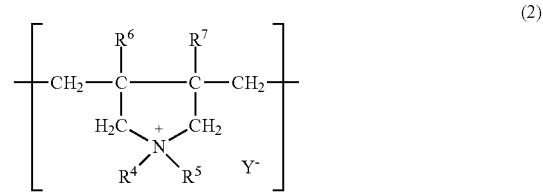

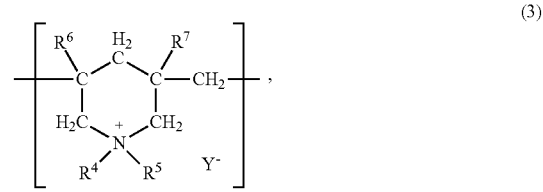

wherein $R^4$ and $R^5$ each independently represent a hydrogen atom, an alkyl group having from 1 to 18 carbon atoms, an aryl group, a hydroxyalkyl group, an amidoalkyl group, a cyanoalkyl group, an alkoxyalkyl group, or a carboalkoxyalkyl group; $R^6$ and $R^7$ each independently represent a hydrogen atom, an alkyl group having from 1 to 3 carbon atoms, or a phenyl group; and $Y^-$ represents an anion, wherein a mass ratio of the component (C) to the component (A), (C)/(A), is from 0.7 to 1.33,
a content of the component (B) is from 0.05% by mass to 10% by mass, and
a content of the component (C) is from 0.035% by mass to 10% by mass.

2. The hair cosmetic according to claim 1, wherein the anionic structural unit of the component (C) comprises a carboxy group.

3. The hair cosmetic according to claim 2, wherein the component (C) is an ampholytic polymer represented by the following formula (4):

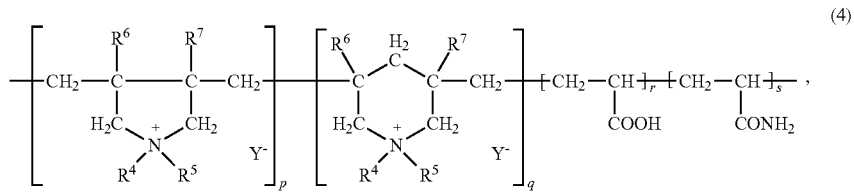

(4)

wherein $R^4$, $R^5$, $R^6$, $R^7$, and $Y^-$ are the same as in claim 1; p, q, r, and s each represent a molar fraction; and (p+q+r+s) is 100, provided that (p+q) is more than 0, and r is more than 0.

4. The hair cosmetic according to claim 3, wherein in the formula (4), (p+q) is from 5 to 95; r is from 5 to 95; and s is from 0 to 70.

5. The hair cosmetic according to claim 1, wherein a pH is from 8.0 to 12.0.

6. The hair cosmetic according to claim 1, wherein a content of the component (A) is from 0.05% by mass to 5% by mass.

7. The hair cosmetic according to claim 1, further comprising:
(D) an anionic surfactant.

8. The hair cosmetic according to claim 7, which is a hair cleansing agent.

9. A method of dyeing hair, comprising:
applying the hair cosmetic according to claim 1 on hair.

10. The hair cosmetic according to claim 1, wherein the cation charge density of the component (B) is from 0.2 to 2.5 meq/g.

11. The hair cosmetic according to claim 1, wherein the component (B) is at least one selected from the group consisting of a cationized guar gum, a cationized tara gum, a cationized locust bean gum, a cationized polyvinyl alcohol, a cationized hydroxyalkyl cellulose, a vinylpyrrolidone/N,N-dimethylaminoethyl methacrylate diethyl sulfate copolymer, a N,N-dimethylaminoethyl methacrylate diethyl sulfate/N,N-dimethyl acrylamide/dimethacrylic acid polyethylene glycol copolymer, and a vinyl imidazolium trichloride/vinylpyrrolidone copolymer.

12. The hair cosmetic according to claim 1, wherein the component (B) is at least one selected from the group consisting of a cationized guar gum, a cationized tara gum, a cationized locust bean gum, and a cationized hydroxyalkyl cellulose, each having the cation charge density of from 0.2 to 2.5 meq/g.

13. The hair cosmetic according to claim 1, wherein the component (B) is at least one selected from the group consisting of a cationized guar gum, a cationized tara gum, a cationized locust bean gum, and a cationized hydroxyalkyl cellulose.

14. The hair cosmetic according to claim 1, wherein the component (B) is at least one selected from the group consisting of a cationized guar gum, a cationized tara gum, a cationized locust bean gum, and a cationized hydroxypropyl cellulose.

15. The hair cosmetic according to claim 1, wherein the content of the component (C) is from 0.035% by mass to 0.3% by mass.

* * * * *